United States Patent
Zhang et al.

(10) Patent No.: US 11,571,258 B2
(45) Date of Patent: Feb. 7, 2023

(54) PATH PLANNING METHOD WITH ARTIFICIAL POTENTIAL FIELD BASED ON OBSTACLE CLASSIFICATION AND MEDICAL SYSTEM FOR STEERING FLEXIBLE NEEDLE

(71) Applicants: BEIHANG UNIVERSITY, Beijing (CN); SHENZHEN FITCARE ELECTRONICS CO., LTD., Shenzhen (CN)

(72) Inventors: Hui Zhang, Beijing (CN); Zhi Qi, Beijing (CN); Yuedong Cao, Shenzhen (CN); Xiaobao Chen, Shenzhen (CN)

(73) Assignees: BEIHANG UNIVERSITY, Beijing (CN); SHENZHEN FITCARE ELECTRONICS CO., LTD., Shenzhen (CN)

( * ) Notice: Subject to any disclaimer, the term of this patent is extended or adjusted under 35 U.S.C. 154(b) by 395 days.

(21) Appl. No.: 16/854,583

(22) Filed: Apr. 21, 2020

(65) Prior Publication Data
US 2020/0330159 A1    Oct. 22, 2020

(30) Foreign Application Priority Data

Apr. 22, 2019   (CN) .......................... 201910324443.9

(51) Int. Cl.
*A61B 34/10*    (2016.01)
*A61B 90/11*    (2016.01)
(Continued)

(52) U.S. Cl.
CPC .............. *A61B 34/10* (2016.02); *A61B 90/11* (2016.02); *G06T 1/0014* (2013.01); *G06V 20/10* (2022.01);
(Continued)

(58) Field of Classification Search
None
See application file for complete search history.

(56) References Cited

U.S. PATENT DOCUMENTS

2017/0071672 A1* 3/2017 Shochat ............... A61B 6/5235
2020/0060772 A1* 2/2020 Konh .................... A61B 34/20

OTHER PUBLICATIONS

Minhas et al., "Modeling of Needle Steering via Duty-Cycled Spinning", Proceedings of the 29th Annual Int'l Conference of the IEEE EMBS, Lyon, France, Aug. 23-26, 2007.

\* cited by examiner

*Primary Examiner* — Kyle Zhai
(74) *Attorney, Agent, or Firm* — Pai Patent & Trademark Law Firm; Chao-Chang David Pai (57) ABSTRACT

An artificial potential field path planning method and an apparatus based on obstacle classification solve the problem of path and motion uncertainty in steering a flexible needle in soft tissue. The apparatus includes an image sensing system, a control module, an execution system and an upper PC. Using the apparatus, the method includes: the image sensing system obtains real-time images of the puncture environment, identifies a target and obstacles from the real-time images, classifies the obstacles, and calculates total potential energy of points in the current environment based on artificial potential field. With a curvature constraint and an optimization index for the flexible needle, the path planning module carries out static path planning to obtain an initial path and the needle entry point, then conducts dynamic path planning to determine the path for steering the flexible needle in the soft tissue accordingly.

5 Claims, 5 Drawing Sheets

(51) Int. Cl.
*G16H 30/40* (2018.01)
*A61B 34/30* (2016.01)
*A61B 17/00* (2006.01)
*G16H 20/40* (2018.01)
*G16H 40/63* (2018.01)
*G06T 1/00* (2006.01)
*G06V 20/10* (2022.01)

(52) U.S. Cl.
CPC ............. *G16H 20/40* (2018.01); *G16H 30/40* (2018.01); *G16H 40/63* (2018.01); *A61B 2017/00398* (2013.01); *A61B 2034/107* (2016.02); *A61B 2034/301* (2016.02)

PATH PLANNING METHOD WITH ARTIFICIAL POTENTIAL FIELD BASED ON OBSTACLE CLASSIFICATION AND MEDICAL SYSTEM FOR STEERING FLEXIBLE NEEDLE

BACKGROUND OF THE INVENTION

1. Field of the Invention

The present invention is directed to the field of soft tissue puncture surgery, and in particular to a path planning method and a system for steering a flexible needle in robot automatic puncture surgery.

2. Description of the Related Field

As a kind of typical minimally invasive technique, puncture surgery has been widely used in biopsy, drug injection, local anesthesia, close radiotherapy, thermal ablation treatment, and has obtained good results in diagnosis and treatment of many diseases. Because of its small trauma, quick recovery and reduced pain, it has received widespread attention in medical research and applications. In recent years, puncture surgery has made great progress through the cooperation with imaging, sensing and other technologies.

At present, the traditional puncture surgery is mainly carried out by experienced doctors or medical technicians. The puncture instrument and human tissue information, which are provided by medical detecting and monitoring equipment, are combined with the experience of the medical personnel to meet the entire surgical requirements. However, due to the limitation of equipment performance, the complex internal environmental conditions of patients and the constraints of medical technician on physical strength, experience and other factors, puncture surgery usually has some deficiencies, such as low puncture accuracy and greater pain of patients.

In order to solve the above problems, a lot of prior research has been done. Due to the complexity of the human body environment, soft tissue organs such as the vital organs, nerves, blood vessels, are irregularly distributed. The shape of the rigid needle puncture path is close to a straight line, and sometimes the needle cannot reach the target position without damaging such important organs. Research has shown that the bevel tip flexible puncture needle can change the path shape by the interaction between the needle and the tissues. By changing the shape of the needle, the target position can be reached by avoiding the main tissues and organs. In order to overcome the subjective problems of medical technicians, such as the differences in physical strength and surgical technique, the puncture medical robot system has been put forward. With the introduction of closed loop control system, the puncture accuracy will be improved significantly, and physicians can put the primary focus on observation and judgment of patient's conditions. At the same time, accurate rapid puncture surgery can reduce the patients' pain and the risk of complications. By integrating the accurate control of the automatic control system for flexible needle and the experience of the medical staff, the scope of application and surgical efficiency of puncture surgery will be greatly expanded.

Flexible needle path planning is a primary problem of the medical robot system control. Most of above strategies use the traditional path planning methods. Although it is possible to realize a geometric path, but the traditional path planning methods usually do not consider the kinematic characteristics of the flexible needle, the disparities in body's internal environment and the real-time operation requirements of the system, therefore there are many limitations of the traditional path planning methods. Due to differences in importance and self-restoring capacity of human organs, some organs cannot be damaged, and some can accept limited tissue damage, so the traditional barriers model may lead to loss or even no solution of the optimal solution and therefore influence puncture treatment. However, only through a unified optimization index is insufficient to shed light on the specific influence on actual path by the various components of the optimization index. For example, the method of rapidly expanding random search tree has the problem of solving instability and deviation from the optimal solution. In addition, the complex mechanism of needle-tissue interaction and the large uncertainty in motion demand higher requirements for tracking control, thus presenting greater difficulties for the stability control of the system.

BRIEF SUMMARY OF THE INVENTION

The invention provides an artificial potential field path planning method and a system for steering flexible needle in soft tissue, based on obstacle classification and the characteristics of flexible needles in order to overcome the uncertainty in path planning and needle motion. For the flexible needle puncture robot path planning method based on soft tissue environment, the present invention establishes a potential energy function based on soft tissue characteristics, and provides an optimization index considering the kinematic characteristics of the flexible needle to improve the trackability of the planned path.

The invention provides a system for steering flexible needle in soft tissue with an artificial potential field path planning strategy based on obstacle classification. The system of the present invention includes an image sensing system, a control module, an execution system and an upper computer. The image sensing system includes a sensor and an image processing module. The control module includes a path planning module and a tracking control module. The execution system includes an actuator driver and a number of actuators. The actuators include a rotating motor controlling the rotating motion and a linear feeding motor controlling the linear motion of the flexible needle.

The sensor is used to acquire the position of the flexible needle and the image data of the puncture environment in real time. Then the sensor transmits the information to the image processing module. The image processing module identifies the target point and obstacles from the image data, obtains the classification factors of the obstacles according to a pre-stored parameter database, and divides the puncture environment into image nodes based on the requirements of puncture accuracy. Each of the image nodes corresponds to a position point in the current puncture environment of the flexible needle, and the total potential energy is obtained for each position point. The control module is installed in an embedded control system. According to the curvature constraint and optimization index of the path planning strategy, the path planning module conducts a static path planning based on the total potential energy of the position points in the current puncture environment, and obtains a static path S and a needle entry point a. Based on the needle entry point a, the tracking control module identifies obstacles in the current puncture environment in real time through the sensor and the image processing module. Then the tracking control module corrects the coordinates of position points of the static path S, and sends control instructions to the actuator driver. The actuator driver follows the control instructions to drive the actuators. The actuators then steers the flexible needle to move in the soft tissue. The upper computer is used for monitoring, coordinating and debugging each of the components of the system.

By implementing the above system, the invention provides an artificial potential field path planning method based on obstacle classification for steering flexible needle, including the following steps:

Step 1: the sensor obtains the real-time images of the puncture environment of the flexible needle;

Step 2: the image processing module identifies the target point b and the obstacles in the puncture environment from the images obtained in Step 1, and obtains the classification factors of the obstacles according to a pre-stored parameter database. The image processing module divides the puncture environment into image nodes according to the requirements of puncture accuracy. Then the image processing module obtains the potential energy of each position point in the puncture environment.

Step 3: according to the curvature constraint and optimization index of the path planning strategy, the path planning module carries out an inverse static path planning starting from the target point b based on the potential energy of each position point in the current puncture environment, and obtains a static path S and the needle entry point a.

The curvature constraint of the flexible needle path is: flexible needle deformation curvature $K<K_m$; and the optimization index of flexible needle path planning is $J=J_1+J_2+J_3$;

where $K_m$ is the maximum curvature, $J_1$ is a curvature optimization factor, s represents the path length, and $K(s)$ is the function of curvature with respect to path length s, $J_2$ is an optimization factor of curvature change rate, $J_3$ is an optimization factor of path length;

Step 4: the sensor obtains the images of the current puncture environment of the flexible needle in real time. The image processing module identifies the obstacles in the current puncture environment, and the tracking control module uses the needle entry point a based on the static path S as the starting point to implement a dynamic forward path planning using the real-time images to repeatedly determine the next path point (as the needle-tip position) until reaching the target point b.

Step 5: the tracking control module sends control instructions to the actuator driver according to the coordinates of the next path point of the path. The actuator driver drives the actuators according to the control instructions, and the actuators steer the flexible needle to move in the soft tissue.

The advantages of the artificial potential field path planning system and method are as follows: the artificial potential field path planning system and method of the present invention minimizes the path uncertainty and motion uncertainty of the flexible needle. By comprehensive consideration of the obstacle characteristics in the puncture environment and the motion of the flexible needle, firstly, the obstacle classification parameters are introduced to artificial potential energy, not only increasing the scope of solving the feasible path to get more puncture paths, but also reducing the difficulty in the implementation of flexible needle. Besides, artificial potential field method has less computational burden, which can improve the real-time performance of the path planning method. By considering the puncture path characteristics of the controlled needle and establishing the corresponding path optimization index, both the feasibility of the planned path and the tracking control accuracy of the flexible needle can be improved.

DETAILED DESCRIPTION OF THE INVENTION

The invention is further described below in conjunction with the attached drawings and examples.

The invention provides a path planning method and a system for steering a flexible needle in puncture surgery based on the artificial potential field and obstacle classification in combination with the kinematics characteristic of the flexible needle. Through the artificial potential field method, the potential energy functions of different tissues are set to realize the differentiation of obstacles. It makes it easier to obtain reasonable paths for the flexible needle. Under the invariable environment condition and the related parameters, the artificial potential field method can generate a stable path, while taking into account the dynamics and meeting the flexible needle puncture operation requirements. Then the method sets up an optimization index function based on the kinematics characteristics of the flexible needle. By considering the kinematics characteristic of the flexible needle in the path planning, feasible paths for the flexible needle can be found.

Figure 1:
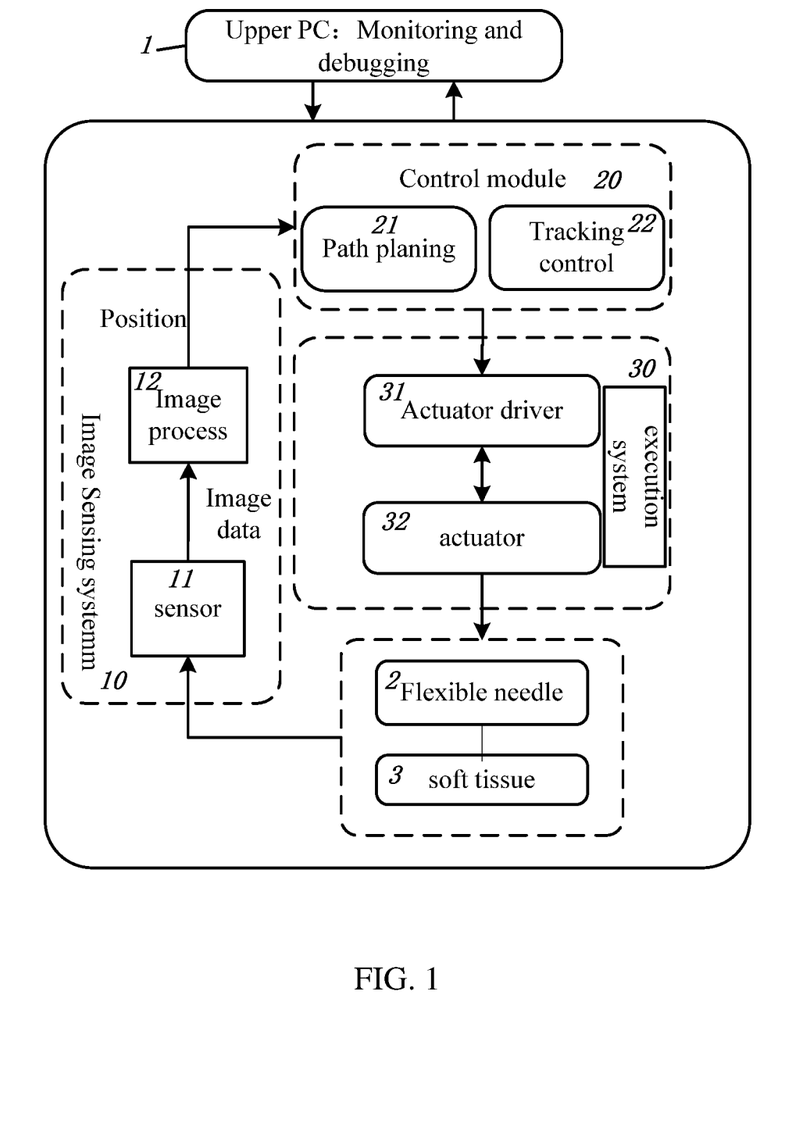
FIG. 1 shows the components of the system for steering flexible needle in puncture surgery according to the present invention.

As shown in FIG. 1, the system for steering flexible needle in puncture surgery according to the present invention includes an upper computer 1, an image sensing system 10, a control module 20, an execution system 30 and a flexible needle 2 to be steered into a soft tissue 3. The image sensing system 10 includes a sensor 11 and an image processing module 12. The sensor 11 is mounted on an extracorporeal scaffold to obtain the image data 13 of the flexible needle position and the puncture environment. Then the sensor 11 transmits the image data 13 to the image processing module 12. The image processing module 12 is installed on an industrial PC or computer, which is used for processing the image data 13 and identifying the target point and obstacles. According to the parameters of a pre-existing classification parameter database, the image processing module 12 obtains classification factors of the obstacles. Based on the requirement of puncture accuracy, the image of the current puncture environment is divided into image nodes, each image node corresponding to a point of the current puncture environment. Then the total potential energy of each point in the puncture environment is obtained. The control module 20 includes a path planning module 21 and a tracking control module 22. The control module 20 receives the target point, the positions of the obstacles and obstacle classification factors from the image processing module 12. The path planning module 21 carries out a static path planning and a dynamic path planning for the flexible needle 2, and the tracking control module 22 carries out dynamic tracking control for the flexible needle 2.

The execution system 30 includes an actuator driver 31 and one or more actuators 32. The actuators 32 mainly include a rotating motor and a linear feeding motor. The rotating motor is used to control the rotating motion of the flexible needle 2, while the linear feeding motor controls the linear motion of the flexible needle 2. The actuator driver 31 amplifies the power according to the reference signal sent by the control module 20 to drive the actuator 32 or motor. And the actuators 32 steer the flexible needle 2 to move in the soft tissue 3. The actuators 32 feed the information back to the actuator driver 31. IO interfaces are set up on the upper computer 1 to connect with other components and for monitoring, coordinating and debugging those components.

Figure 2:
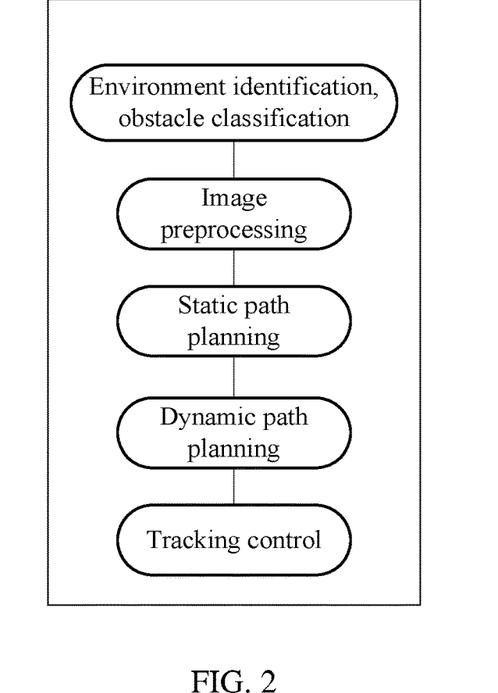
FIG. 2 is the flow diagram of the path planning method for steering flexible needle according to the present invention.

The artificial potential field path planning method of the invention on the one hand adopts the approach of obstacle classification, and on the other hand uses the path planning optimization index in combination with the physical characteristics of the flexible needle 2. The overall process is shown in FIG. 2. Each of the steps is described below.

Step 1: The sensor 11 collects the image data 13 of the puncture environment and transmits the image data to the image processing module 12.

In the invention, the probe of the sensor 11 is fixed outside the soft tissue 3, and the images of the puncture environment can be obtained in real time.

The image processing module 12 analyzes the image data 13 collected and obtains the target environment data by the sensor 11. Firstly, the image processing module 12 preprocesses the overall information of the puncture environment, and then performs real-time puncture commands to match the actual environment to the preprocessed environment.

Step 2: according to the image data 13 collected in Step 1, the image processing module 12 preprocesses the images to identify and match the soft tissue organs using artificial intelligence technology. The obstacles are identified and the boundaries thereof are clearly demarcated according to the soft tissue features.

Based on the above image processing, the system obtains the soft tissue environment of the flexible needle puncture and acquires the target point b. The organs are represented by obstacles, and the target point b is the end position of the puncture. Before planning the path, the image processing module 12 obtains the classification factor r for each obstacle from the obstacle classification factor parameter database. The image processing module 12 divides the images according to the accuracy requirements of puncture control into image nodes, each of which corresponds to a point in the puncture environment. Specifically, the image is rasterized to obtain the points arranged in rows and columns. Based on the traditional artificial potential field path planning method and the obstacle classification factor parameters, the total potential energy of each point in the current puncture environment is obtained. The path is determined according to the total potential energy.

In the invention, according to the importance and recovery ability of each organ, experienced experts classify the obstacles represented by each organ tissue and establish the corresponding parameter database, in which different classes of obstacles correspond to different parameters, expressed as the obstacle classification factor r. The strategy will adjust the gain coefficient of gravity and repulsion potential energy based on r. The larger the r value is, the more important is the tissue or organ represented by the obstacle. Similarly, for the gain coefficient of gravitational potential energy, the smaller the r value is, the better is the puncturability of the tissue, and the greater is the corresponding gravity.

The artificial potential field method is realized by using the idea of forces exerted on each point in the virtual force field. The obstacle exerts a repulsive force on each point of the environment, and the target point exerts a gravitational force on each point in the environment. The combined force of the gravitational force and the repulsive force is used as the accelerating force to calculate the optimal motion. The gravitational field increases with the distance between the position of each point in the environment and the target point, and is directed toward the target point. The repulsion field has a maximum value at the position of the obstacle and decreases monotonously with the increase in the distance between the position of each point and the obstacle.

For a point X in the puncture environment, which is the needle-tip position of the flexible needle at the time t, the total potential energy value is calculated according to the following.

The potential energy function of the gravitational field is:

$$U_{att}(X,t) = \tfrac{1}{2} k_{att}(r)(X-X_g)^2 \tag{1}$$

The gravity function is:

$$F_{att}(X,t) = -\nabla U_{att}(X,t) = -k_{att}(r)|X-X_g| \tag{2}$$

The potential energy function of the repulsion field is:

$$U_{np,i}(X,t) = \begin{cases} \tfrac{1}{2} k_{np,i}(r)\left(\dfrac{1}{X-X_{ob,i}} - \dfrac{1}{\rho_{o,i}}\right)^2, & X-X_{ob,i} \leq \rho_{o,i} \\ 0, & X-X_{ob,i} > \rho_{o,i} \end{cases} \tag{3}$$

The repulsion function is:

$$F_{np,i}(X,t) = \tag{4}$$

$$-\nabla U_{np,i}(X,t) = \begin{cases} -k_{np,i}(r)\left(\dfrac{1}{X-X_{ob,i}} - \dfrac{1}{\rho_{o,i}}\right) \dfrac{1}{(X-X_{ob,i})^2} \dfrac{\partial(X-X_{ob,i})}{\partial X}, & X-X_{ob,i} \leq \rho_{o,i} \\ 0, & X-X_{ob,i} > \rho_{o,i} \end{cases}$$

where each variable is the value at time t, i is the obstacle index, $X_g$ is the target point position, and $X_{ob,i}$ is the position of obstacle i, $U_{att}(X,t)$ is the gravitational potential energy at position X, $U_{np,i}(X,t)$ is the repulsive potential energy at position X, $F_{att}(X,t)$ is the gravitational force at position X, and $F_{np,i}(X,t)$ is the repulsive force at position X. The obstacle classification factor is r, $k_{att}(r)$ is the gain coefficient of gravitational potential energy, $k_{np,i}(r)$ is the repulsive potential energy gain coefficient of obstacle i. The maximum value of the action range of obstacle repulsive force is $\rho_{o,i}$. $\nabla$ is a hamiltonian operator. $X-X_{ob,i}$ represents the distance between X and the obstacle i. $X-X_g$ represents the distance between X and the target point $X_g$. The symbol $\partial$ represents the partial derivative.

The obstacles surrounding a point in the puncture environment may be different from point to point, and the corresponding classification factor r of the obstacles may not be the same. When an obstacle is not penetrable or the corresponding tissue is difficult to pierce due to its complex characteristics, the gravitational potential energy of the point has a lower value, for which the gain coefficient with a correspondingly lower value may be represented by katt (r)=εr, where ε is the scale factor of gravitational force, and is a coefficient obtained based on the above features and dimensional requirements. At the same time, the gain coefficient of repulsive potential energy corresponds to a higher value and may be represented by $k_{np,i}$ (r)=ηr, where η is the scale factor of repulsive force, and is a coefficient obtained based on the above characteristics and dimensional requirements. The larger the value of η, the larger is the repulsion potential energy at this point. On the contrary, when an obstacle can be partially penetrated, or its corresponding tissue is stable and easy to penetrate, the gain coefficient of gravitational potential energy $k_{att}(r)$ corresponds to a higher value, and the gain coefficient of repulsive potential energy $k_{np,i}(r)$ corresponds to a lower value. In the strategy, the corresponding values of η and ε are set by the expert for the classification factor r of each obstacle in advance. This can ensure that the above gravitational field and repulsion field have proper values and directions.

The total potential energy at time t is expressed as follows:

$$U(X, t) = U_{att}(X, t) + \sum_{i=1}^{N} U_{np,i}(X, t) \quad (5)$$

where N is the total number of obstacles.

The sum of gravitational potential energy and repulsive potential energy is the total potential energy at the point. According to the potential energy function, the total potential energy at each point in the soft tissue environment is calculated. Due to the influence of the classification factor r, the obstacle will have different gravitational and repulsion potential energy, and then path planning based on obstacle classification factors can be realized.

Step 3: the method establishes the optimization index based on the kinematics of the flexible needle puncture, obtains the needle entry point by combining the potential energy function of each point in the environment, and carries out the static path planning.

Figure 3:
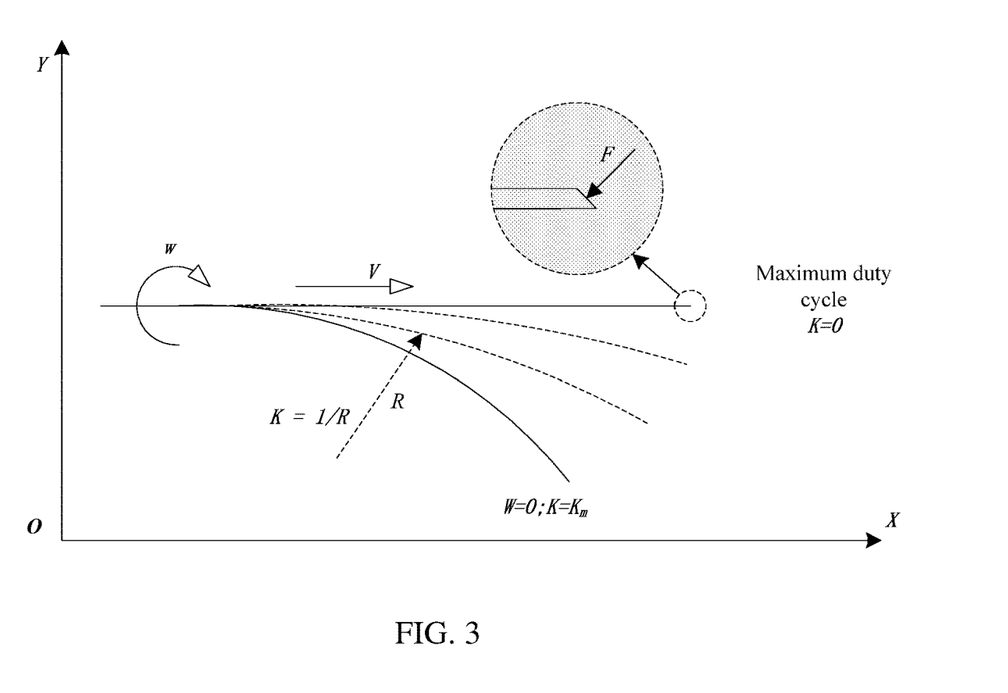
FIG. 3 is the kinematics schematic diagram of the flexible needle puncture according to the present invention.

The kinematics of the flexible needle puncture is shown in FIG. 3. The movement of the flexible needle 2 is composed of a rotational motion of the needle body caused by the rotating motor and a linear feeding motion caused by the feeding motor. After the flexible needle 2 is inserted into a soft tissue 3, the flexible needle 2 will receive a force. When the needle body is fed at the feed speed V, it will encounter a normal force F on the bevel tip, and the deformation of the flexible needle 2 will cause a rotating motion with a radius R. According to prior study, it has been found that the deformation curvature, K=1/R, is only related to the intrinsic characteristics of flexible needle 2, and it has no relationship with other factors such as feed speed. In FIG. 3, W is the rotational angular speed of the flexible needle 2, the rotational speed of the rotating motor is 0, and the maximum duty cycle is 1. The maximum duty cycle is the duty cycle given by the actuator driver 31 at the maximum rotational speed of the rotating motor.

Based on the above principle, Minhas et al (Minhas D S, Engh J A, Fenske M M, et al. Modeling of needle steering via duty-cycled spinning. [J]. 2007) put forward the method of controlling the flexible needle rotational angular speed W and the feed speed V to cause the deformation curvature K of the flexible needle 2 to change continuously from 0 to $K_m$, thus realizing the tracking control. But that imposes new requirements for the path planning.

Based on the physical characteristics of the flexible needle 2, the corresponding optimization indexes are proposed in path planning as follows:

Due to the thin diameter and low stiffness of the flexible needle 2, it is not easy to control when the rotational angular speed is high, so the curvature should be as small as possible. Therefore, the curvature optimization index $J_1$ is:

$$J_1 = \int K(s)^2 ds \quad (6)$$

where s stands for path length, K(s) is the function of curvature with respect to path length.

Due to the continuous interaction between the flexible needle 2 and the surrounding soft tissue during the rotation, the state of the needle tip is unstable when the curvature changes greatly. So the rate of curvature change should be as small as possible. Therefore, the optimization index $J_2$ of the rate of curvature change is:

$$J_2 = \int \dot{K}(s)^2 ds \quad (7)$$

where $\dot{K}(s)$ is the first derivative of the curvature function.

Under the condition that the soft tissue is not damaged, the puncture distance should be as short as possible, so the path length optimization index $J_3$ is:

$$J_3 = \int s^2 ds \quad (8)$$

Considering the physical characteristics of the flexible needle 2, the maximum curvature constraint of the planned path is $K_m$, then $$K < K_m \quad (9)$$

From the above conditions, the curvature constraint and optimization index J of flexible needle path planning can be written as follows:

$$J = J_1 + J_2 + J_3$$

$$K < K_m \quad (10)$$

Figure 4:
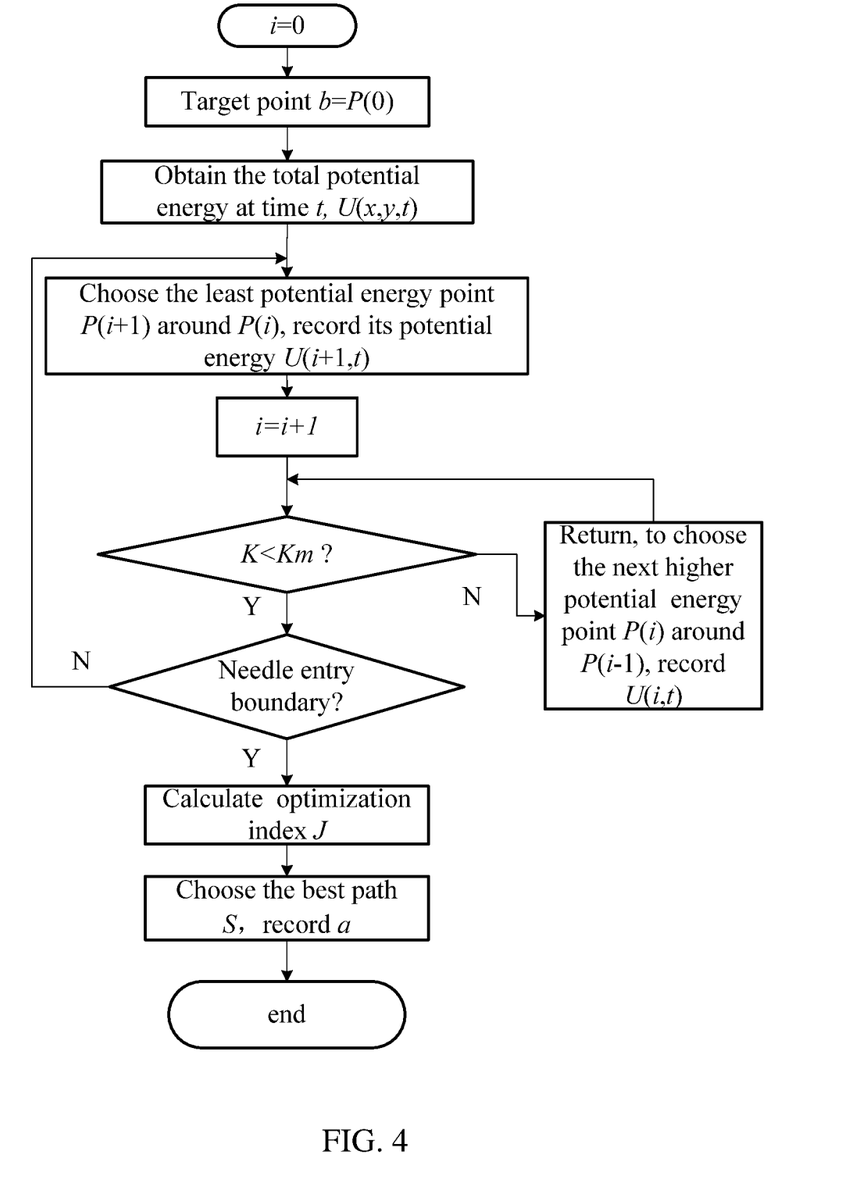
FIG. 4 is the flow diagram of the inverse static path planning according to the path planning method of the present invention.

As shown in FIG. 4, according to formula (1)~(5), the image processing module 12 calculates the overall potential energy U(x,y,t) of each point (x,y) in the inertial coordinate system where the flexible needle 2 is positioned, as shown in FIG. 3 at the moment t. After the environmental recognition provides results of target point b, the position of each obstacle, the classification factor r and the total potential energy of each point, the path planning module 21 calculates the position of the needle entry point a by conducting an inverse static path planning. This process includes Steps 3.1~3.7 as follows.

Step 3.1: define the target point b as the starting point of the path, namely, set target point b as the first point P(0) of the path, and take P(0) as the current point P(i), with i initially set to 0.

Step 3.2: take the current point P(i) as the center, select the point with the lowest total potential energy among the surrounding points as the next point P(i+1) of the path, and record the potential energy U(i+1,t) of the point P(i+1); increase i by 1 and set n=i.

Step 3.3: connect the points P(0), P(1) . . . P(n) obtained so far for the path, where the total number of points of the path is n+1, n is a positive integer, in order to calculate the curvature K of the path and the path length s. The path planning module 21 will judge whether the curvature K meets the curvature constraint (9). If not satisfied, set the current point P(n) to P(i), and go to Step 3.4, otherwise, go to Step 3.6.

Step 3.4: decrease i by 1 and set P(i) as the current point.

Step 3.5: based on the total potential energy surrounding the P(i), choose the point which possesses the next larger total potential energy, increase i by 1 and set n=i, and go to Step 3.3.

Step 3.6: judge whether point P(i) reaches the outer boundary of the soft tissue 3. If the outer boundary is not reached, go to step 3.2 to search for the next path point of the path; otherwise, the static path planning is completed and P(i) is set to the needle entry point a.

Step 3.7: in the process on looking for the next path point from P(i), it is likely to find more than one surrounding point possessing a same minimum potential energy. If so, more than one path will be generated. In that case, the optimization index J is used to evaluate the paths generated. The path planning module 21 calculates the J value of each path, selects the path with the least J value as the final static path S, and records the corresponding needle entry point a.

The outer boundary of where a is located is an open boundary, so the inverse method is adopted, from the target point b to the needle entry point a.

Figure 5:
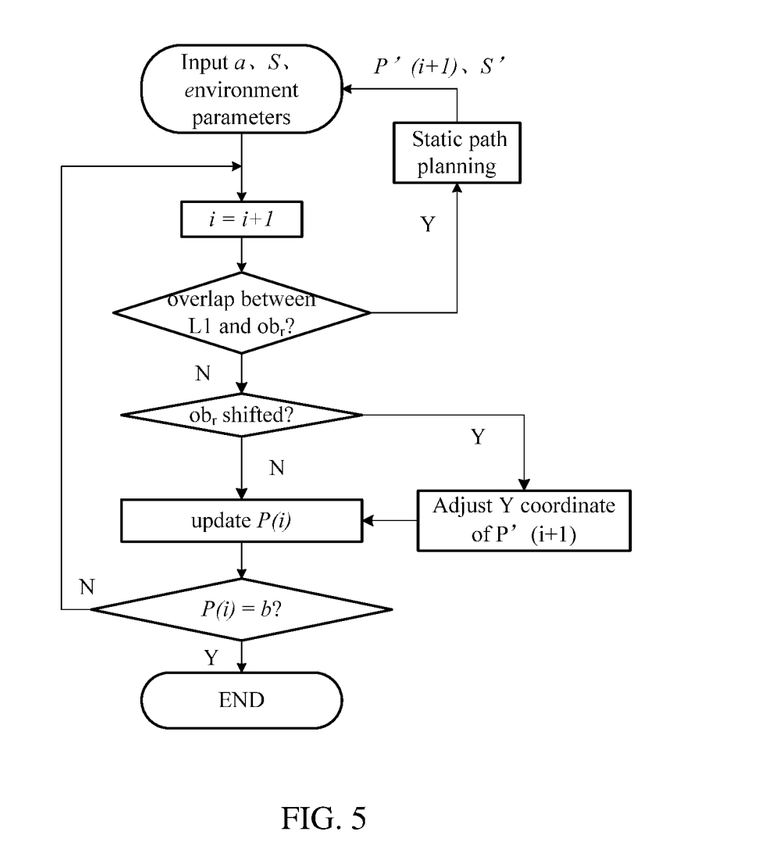
FIG. 5 is the flow diagram of the dynamic forward path planning according to the path planning method of the present invention.

Step 4: the path planning module 21 determines the actual surgical needle entry point a based on the static path planning, and implements the actual path according to the results from real-time image processing until the target point b is reached. The specific process is shown in FIG. 5 including Steps 4.1 to 4.5 explained below. The needle entry point a (specifying the initial needle-tip position of the flexible needle 2) is determined by the static path planning and will be used as the first path point in the dynamic forward path planning process.

Figure 6:
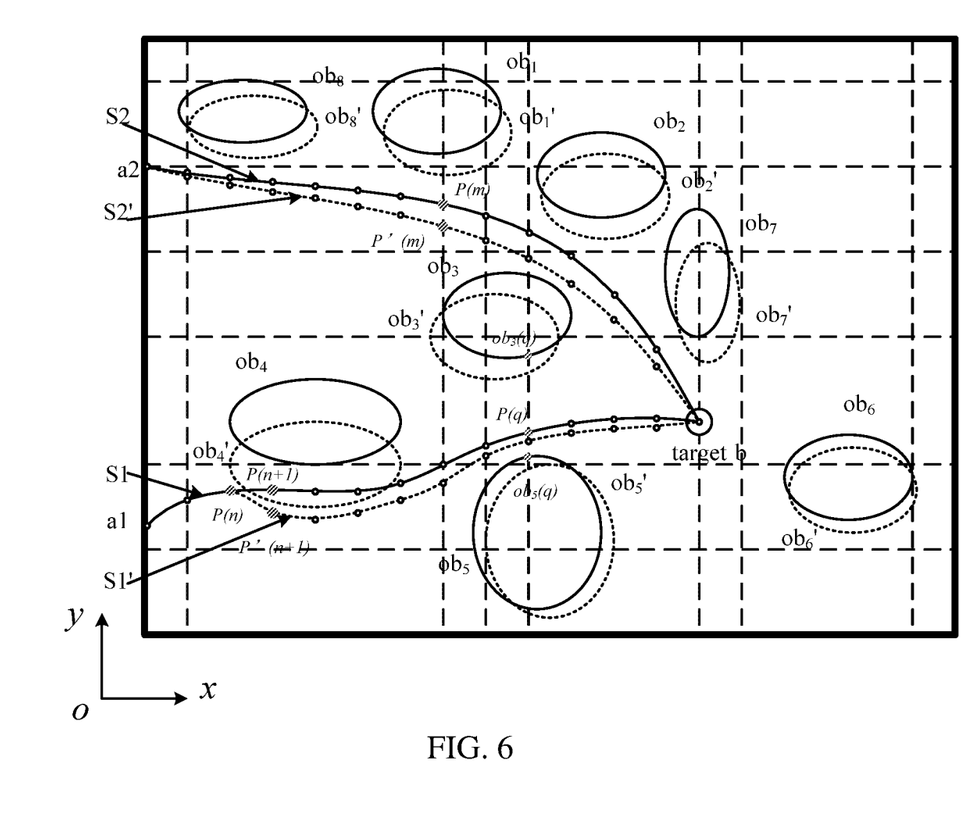
FIG. 6 is a schematic diagram of two examples to illustrate dynamic path planning method of the present invention

FIG. 6 shows two examples paths S1, S2 from static path planning and the corresponding paths S1', S2' obtained from the dynamic forward path planning to illustrate how the path points are determined or adjusted/corrected in the dynamic forward path planning. FIG. 6 shows a simulated puncture environment with 8 obstacles $ob_1$-$ob_8$. Each obstacle position is represented by its centroid coordinate, which is used to calculate the repulsive potential energy. The target coordinate is the centroid coordinate of the target point b. The contour coordinates of each obstacle are obtained by the image sensing system 10. Besides, the grid formed by each dotted line is the coordinate grid of the image, and the coordinate precision depends on the surgical requirements and the state of the equipment.

Step 4.3 and step 4.4 are explained and illustrated using the two examples shown in FIG. 6. According to step 4.1, the entry points a1, a2 and the initial paths S1 and S2 are obtained by static path planning respectively. During the operation, the puncture environment will change with the shift in the positions of $ob_1$-$ob_8$, due to the patient's posture, physiological respiration or other factors, to the new positions are $ob_1'$-$ob_8'$. The S1' and S2' are the actual paths obtained by dynamic forward path planning after the obstacle position changes.

According to Step 4.3, when obstacle $ob_4$ shifts its position, the path S1 obtained by static path planning intersects $ob_4'$ between P(n) and P(n+1). In order to address the problem, a new path S1' is obtained by the static path planning with P(n) as the starting point and the target point a as the end point. As a result, the next path point P(n+1) is changed to the point P(n+1)'.

On the other hand, according to Step 4.4, when obstacles $ob_1$-$ob_8$ shift their positions, the relative position of path S2 obtained by static path planning changes with each obstacle. It is necessary to adjust the path points of the path S2. And the significant influence on the new adjusted path is from the obstacles adjacent to the current path point of the path S2. For the point P(m), although the adjacent obstacles shift in position, there is no crossing between the path S2 and the adjacent obstacles. Considering the computational burden, it is needless to replan the path. The new position for point P(m) is adjusted according to its position relative to the boundaries of adjacent obstacles $ob_1$ and $ob_3$, to eventually obtain P'(m). For example, the Y-coordinate of P(m) may be adjusted by the distance by which the boundary of an adjacent obstacle has shifted in the Y-direction at the same X-coordinate as that of P(m). The new position for P(m) is P'(m). According to this idea, each point on the path is iterated in turn, and the new path S2' is finally obtained.

Where the adjacent obstacle contour points are defined as the points at the same X-coordinates with the current path point and the smallest difference of Y-coordinates to the obstacle edges in both Y-axis directions. For example, in FIG. 6, the $ob_3(p)$ and $ob_5(p)$ are the adjacent obstacle contour points of P(q).

Step 4.1: according to the step 3, the needle entry point a and the initial reference path S are obtained, and the position and boundary of each obstacle in the current environment are obtained from the real-time images obtained by the sensor 11 and analyzed by the image processing module 12.

Step 4.2: identifying a reference obstacle $ob_r$ that is closest to the current path point P(i) among the obstacles, and determining whether a line section L1 connecting the current path point P(i) and the next path point P(i+1) of the reference path has an overlap with any of the obstacles;

Step 4.3: if any overlap is determined in step 4.2, then conducting a static path planning starting from the current path point P(i) to the target point b to yield an updated static path S' and setting the next path point P'(i+1) of the dynamic path to the path point of the static path following the current path point P(i); then updating the current path point P(i) and setting the updated static path as the reference path S.

Step 4.4: if no overlap is determined in step 4.2, then measuring a distance in the y direction, at the same x-coordinate as the next path point P'(i+1) of the reference path S, by which the reference obstacle $ob_r$ has shifted since the reference obstacle was previously identified, and setting the next path point P'(i+1) of the dynamic path to a point that is the next path point of the reference path with its y-coordinate adjusted by the distance; then updating the current path point;

Step 4.5: if the current path point P(i) of the dynamic path is not the target point, repeating steps 4.2 to 4.4; otherwise ending Step 4.

Step 5: according to the path position coordinate, the tracking control module 22 calculates specific control commands for corresponding actuators 32, including the rotating motor and the feeding motor. Then the control 30 sends the commands to the actuator driver 31 to drive the rotating motor and the feeding motor to steer the flexible needle 2.

What is claimed is:

1. An apparatus for steering a flexible needle in soft tissue using artificial potential field path planning strategy based on obstacle classification, the apparatus comprising an image sensing system, a control module, an execution system and an upper computer, wherein the image sensing system includes a sensor and an image processing module, the control module includes a path planning module and a tracking control module, the execution system includes an actuator driver and a plurality of actuators;

the sensor is disposed for acquiring in real time a current position of the flexible needle and images of a puncture environment in the soft tissue, and transmitting the current position and the images to the image processing module;

the image processing module is disposed for identifying from the images a target point and obstacles in the puncture environment, obtaining classification factors of the obstacles according to a pre-stored classification parameter database, and calculating total potential energy at certain points in the puncture environment;

the path planning module is disposed for conducting static path planning and dynamic path planning with a curvature constraint and an optimization index and based on the total potential energy, wherein the static path planning is conducted to obtain a static path, starting from the target point and ending at a needle entry point at an outer boundary of the soft tissue; the dynamic path planning is conducted to determine a dynamic path including a plurality of path points, starting from the needle entry point and ending at the target point, using the images obtained in real time by the image sensing system;

the tracking control module is disposed for transmitting a control instruction to the actuator driver at each of the path points determined for the dynamic path; and the actuator driver is disposed for following the control instruction to drive the plurality of actuators to steer the flexible needle in the soft tissue.

2. The apparatus for steering a flexible needle in soft tissue as claimed in claim 1, wherein the image processing module obtains the total potential energy of each point in the puncture environment as follows:

for each point at position X, the total potential energy at time t, expressed as U(X,t), is:

$$U(X, t) = U_{att}(X, t) + \sum_{i=1}^{N} U_{np,i}(X, t)$$

where N is the total number of the obstacles in the puncture environment, $U_{att}(X,t)$ is a gravitational potential energy at point X, and $U_{np,i}(X,t)$ is a repulsive potential energy at point X with respect to obstacle i, according to the following formulas:

$$U_{att}(X, t) = \frac{1}{2} k_{att}(r)(X - X_g)^2;$$

$$U_{np,i}(X, t) = \begin{cases} \frac{1}{2} k_{np,i}(r) \left( \frac{1}{X - X_{ob,i}} - \frac{1}{\rho_{o,i}} \right)^2, & X - X_{ob,i} \leq \rho_{o,i} \\ 0, & X - X_{ob,i} > \rho_{o,i} \end{cases}$$

where $X_g$ is the position of the target point, $X_{ob,i}$ is the position of obstacle i, r is the obstacle classification factor, $\rho_{o,i}$ is the maximum value of the action range of the obstacle repulsive force of obstacle i, $k_{att}(r)$ is the gain coefficient of the gravitational potential energy, and $k_{np,i}(r)$ is the repulsive potential energy gain coefficient of obstacle i.

3. The apparatus for steering a flexible needle in soft tissue as claimed in claim 1, wherein for the static path planning conducted by the path planning module the curvature constraint is:

$$K(s) < K_m,$$

where K(s) is a deformation curvature of the flexible needle with respect to path length s, $K_m$ is the maximum deformation curvature; and the optimization index (J) is obtained according to:

$$J = J_1 + J_2 + J_3,$$

where $K_m$ is the maximum deformation curvature, $J_1$ is a curvature optimization index, $J_2$ is a curvature change rate optimization index, and $J_3$ is a path length optimization index.

4. The apparatus for steering a flexible needle in soft tissue as claimed in claim 1, wherein the plurality of actuators includes a rotating motor for controlling rotating motion of the flexible needle and a linear feeding motor for controlling linear motion of the flexible needle.

5. The apparatus for steering a flexible needle in soft tissue as claimed in claim 1, wherein the puncture environment is divided and arranged in a lattice of image nodes based on requirements of puncture accuracy, each of the image nodes corresponding to a point in the puncture environment, and only such a finite number of points are considered for the path planning and total potential energy calculation.

* * * * *